United States Patent
Knappke-Bongartz et al.

(10) Patent No.: US 11,702,385 B2
(45) Date of Patent: Jul. 18, 2023

(54) UREA GROUP CONTAINING ANTI-SAGGING RHEOLOGY CONTROL AGENTS

(71) Applicant: BYK-Chemie GmbH, Wesel (DE)

(72) Inventors: Christiane Knappke-Bongartz, Wesel (DE); René Nagelsdiek, Wesel (DE); Sylvia Bühne, Wesel (DE); Agnetha Klein, Wesel (DE); Berthold Jacobs, Wesel (DE)

(73) Assignee: BYK-Chemie GmbH, Wesel (DE)

( * ) Notice: Subject to any disclaimer, the term of this patent is extended or adjusted under 35 U.S.C. 154(b) by 395 days.

(21) Appl. No.: 16/955,430

(22) PCT Filed: Dec. 20, 2018

(86) PCT No.: PCT/EP2018/086357
§ 371 (c)(1),
(2) Date: Jun. 18, 2020

(87) PCT Pub. No.: WO2019/122222
PCT Pub. Date: Jun. 27, 2019

(65) Prior Publication Data
US 2021/0070697 A1    Mar. 11, 2021

(30) Foreign Application Priority Data
Dec. 21, 2017 (EP) .................................. 17209527

(51) Int. Cl.
| | | |
|---|---|---|
| C09D 175/02 | (2006.01) | |
| C08G 18/10 | (2006.01) | |
| C08G 18/79 | (2006.01) | |
| C07C 275/24 | (2006.01) | |
| C09D 7/43 | (2018.01) | |
| C07C 275/18 | (2006.01) | |
| C08G 18/24 | (2006.01) | |
| C08G 18/28 | (2006.01) | |
| C08G 18/40 | (2006.01) | |
| C08G 18/76 | (2006.01) | |
| C09D 4/00 | (2006.01) | |
| C09D 175/04 | (2006.01) | |
| C08G 18/71 | (2006.01) | |
| C08G 18/32 | (2006.01) | |

(52) U.S. Cl.
CPC .......... *C07C 275/24* (2013.01); *C07C 275/18* (2013.01); *C08G 18/10* (2013.01); *C08G 18/24* (2013.01); *C08G 18/2825* (2013.01); *C08G 18/3228* (2013.01); *C08G 18/4063* (2013.01); *C08G 18/71* (2013.01); *C08G 18/714* (2013.01); *C08G 18/7614* (2013.01); *C08G 18/792* (2013.01); *C09D 4/00* (2013.01); *C09D 7/43* (2018.01); *C09D 175/02* (2013.01); *C09D 175/04* (2013.01)

(58) Field of Classification Search
CPC ............ C08G 18/2825; C08G 18/3228; C08G 18/71; C08G 18/714; C08G 18/7614; C08G 18/10
See application file for complete search history.

(56) References Cited

U.S. PATENT DOCUMENTS

| | | | | |
|---|---|---|---|---|
| 3,766,070 | A | * | 10/1973 | Wulfers ............... C10M 115/08 508/464 |
| 4,311,622 | A | | 1/1982 | Buter |
| 4,677,028 | A | | 6/1987 | Heeringa et al. |
| 5,554,586 | A | | 9/1996 | Pratt |
| 6,617,468 | B2 | | 9/2003 | Haubennestel |
| 7,250,487 | B2 | | 7/2007 | Tournilhac |
| 7,348,397 | B2 | | 3/2008 | Tournilhac |
| 9,458,332 | B2 | | 10/2016 | Leutfeld |
| 2002/0115882 | A1 | | 8/2002 | Haubennestel |
| 2004/0127674 | A1 | | 7/2004 | Haubennestel |
| 2004/0158022 | A1 | | 8/2004 | Baumgart et al. |
| 2005/0182205 | A1 | | 8/2005 | Guha et al. |
| 2012/0226075 | A1 | * | 9/2012 | Leutfeld ............. C08G 18/706 564/59 |
| 2017/0037262 | A1 | | 2/2017 | Leutfeld |

FOREIGN PATENT DOCUMENTS

| | | |
|---|---|---|
| CN | 1338453 | 3/2002 |
| CN | 102597036 | 7/2012 |

(Continued)

OTHER PUBLICATIONS

International Search Report and Written Opinion for International Application No. PCT/EP2018/086357 dated Mar. 28, 2019.

(Continued)

*Primary Examiner* — Michael L Leonard
(74) *Attorney, Agent, or Firm* — Fitch, Even, Tabin & Flannery, LLP

(57) ABSTRACT

The present invention relates to a urea group containing product comprising one or more species of formula (I) $R^1$—X—(C=O)—[NH—$R^2$—NH—(C=O)—NH—$R^3$—NH—(C=O)]$_n$—NH—$R^2$—NH—(C=O)—X—$R^1$ (I), wherein $R^1$ is independently selected from organic groups having (4) to (200) carbon atoms, X is O or $NR^4$, wherein $R^4$ is a hydrogen atom or an aliphatic or aromatic group having (1) to (30) carbon atoms, $R^2$ is independently selected from hydrocarbyl groups having (4) to (40) carbon atoms, $R^3$ is independently selected from hydrocarbyl groups having (2) to (40) carbon atoms, and wherein on average (76) to (100) mol % of all $R^3$ groups contained in the one or more species of formula (I) are hydrocarbyl groups having (2) or (3) carbon atoms, and n is an integer of (2) to (150). The invention further relates to a method of manufacturing such urea group containing products, liquid compositions containing the same and the use of such liquid compositions as rheology control additives. Furthermore, the invention relates to a process for rheology adjustment adding such liquid composition to semi-finished or final products. The invention also relates to an article coated with the liquid composition.

15 Claims, No Drawings

(56) References Cited

FOREIGN PATENT DOCUMENTS

| | | |
|---|---|---|
| DE | 2822908 | 7/1979 |
| DE | 19919482 | 11/2000 |
| DE | 10126647 | 12/2002 |
| DE | 10241853 B3 | 1/2004 |
| DE | 102008059702 | 6/2010 |
| DE | 102015004640 | 10/2015 |
| EP | 0006252 A1 | 1/1980 |
| EP | 0198519 A1 | 10/1986 |
| EP | 1188779 | 3/2002 |
| EP | 1188779 A1 | 3/2002 |
| EP | 1396510 | 3/2004 |
| EP | 1630191 A2 | 3/2006 |
| EP | 2292675 | 3/2011 |
| EP | 2931771 B1 | 9/2016 |
| EP | 3728363 | 10/2020 |
| GB | 1454414 | 11/1976 |
| JP | H08176268 | 7/1996 |
| JP | H09302062 | 11/1997 |
| JP | 2002105042 | 4/2002 |
| JP | 2004099896 | 4/2004 |
| JP | 2013503953 | 2/2013 |
| KR | 20000075971 | 12/2000 |
| KR | 20020014680 | 2/2002 |
| KR | 20120083393 | 7/2012 |
| WO | 9509201 A1 | 4/1995 |
| WO | WO-9839373 A1 * | 9/1998 ............ C08G 18/10 |
| WO | 0204579 A1 | 1/2002 |
| WO | 0242392 A2 | 5/2002 |
| WO | 2007105258 | 9/2007 |
| WO | 2014111102 | 7/2014 |
| WO | 2015158407 | 10/2015 |
| WO | 2015158794 | 10/2015 |
| WO | 2017017036 A1 | 2/2017 |
| WO | 2019122222 | 6/2019 |
| WO | 2020182944 | 9/2020 |

OTHER PUBLICATIONS

International Search Report and Written Opinion for International Application No. PCT/EP2021/083717 dated Jan. 25, 2022.

* cited by examiner

UREA GROUP CONTAINING ANTI-SAGGING RHEOLOGY CONTROL AGENTS

The invention relates to urea group containing products, their preparation, and their use as rheology control agents (hereinafter also referred to as "rheology additives" or "rheology agents"). Additionally, the invention relates to rheology control agents comprising urea group containing products and their use. The invention further relates to liquid compositions comprising the urea group containing products and to an article coated with the liquid composition.

The rheology of liquid coating systems is controlled using primarily organically modified bentonites, silicas, hydrogenated castor oil, and polyamide waxes. These substances are mostly dry solids, which must be processed to a semi-finished form using solvents and shearing forces, and/or introduced into the liquid coating system by means of targeted temperature control. If these temperatures are not observed, crystallites occur in the finished coating system, and can not only lead to poor rheological performance, but also to defects in the coating.

These rheological auxiliaries frequently lead to instances of clouding and haze in clear, transparent coatings. Moreover, operating with dry, powderous products, which cause dusts during processing, may be technologically unfavorable.

Other solutions for rheology control have been set out in European patent application EP-A-0198519. Here, an isocyanate is reacted with an amine, in the presence of solutions of film-forming resin, to form a urea, which forms microcrystalline, needle-shaped crystals. These film-forming binders, thus modified, are used as rheology control binders and sag-preventing binders, in the form of what are called "sag control agents".

Other proposals for rheology control are described in U.S. Pat. Nos. 4,311,622 and 4,677,028, where polyisocyanates or polyisocyanurates are reacted with monoamines or polyamines in the mandatory presence of a binder, to form polyureas.

WO 02/04579 describes ureas, which are used for thickening fats or oils. These thickeners are prepared by stoichiometric reaction of primary amines with diisocyanates in the fat or oil which is to be thickened.

Patent specification U.S. Pat. No. 5,554,586 likewise describes the thickening of oils in situ. In this case, a mixture of primary monofunctional amines with polyoxyalkylene diamines is reacted with diisocyanates in the oil to be thickened.

US 2005/0182205 and WO 95/09201 both describe the thickening of molding compounds (bulk molding compounds, BMC, and sheet molding compounds, SMC) using urea derivatives that are obtained by reacting isocyanates with diamines or triamines. As the isocyanate component, it is possible to use aliphatic or aromatic diisocyanates, but also reaction products of diisocyanates with polyetherdiols or polyesterdiols. As the amine component, low molecular weight diamines and triamines, and polyamines, are employed. The urea compounds are prepared by mixing the amine component and isocyanate component in the corresponding resin.

The disadvantage of most of the products described in the above prior art is that they always should be prepared in the medium which is to be thickened, and whose rheology they are supposed to influence. The products, therefore, are not independent of the medium to be thickened. They are not stable on storage, but instead exhibit lumps and/or bits after a short time. A further disadvantage is that these thixotroped media often must be prepared with the aid of a pre-gel. This viscous pre-gel must typically be processed immediately after its preparation, since after a prolonged standing time it can no longer be incorporated without disruption. Subsequent correction of completed formulations is therefore not possible. Most of the rheology control agents of the prior art cannot be prepared alone, but only in the presence of film-forming agents. Their usefulness is therefore limited.

EP 1188779 describes a process for preparing a solution which is effective as a thixotropic agent and comprises urea-urethanes, and the use of this solution for the thickening of coating materials. These urea-urethanes are obtained by reacting monohydroxy compounds with an excess of tolylene diisocyanate, removing the unreacted portion of the tolylene diisocyanate from the reaction mixture, and further reacting the resulting monoisocyanate adducts with diamines in a molar ratio of 2:1, in a solvent, to form urea-urethanes. EP-A-0006252 describes analogous urea-urethanes, which are obtained by stoichiometric reaction of monohydroxy compounds with diisocyanates and diamines.

Patent specification DE 10241853 B3 describes polymeric urea-urethanes obtainable by a first reaction of an excess of diisocyanate with a polyol, to form a double-sidedly NCO-terminated urethane polymer, present alongside excess diisocyanate, and subsequent second reaction of the mixture of the double-sided NCO-terminated urethane prepolymer and the excess diisocyanate, on the one hand, and a mixture of a primary monoamine and a primary diamine, on the other. Reaction media used are polar aprotic solvents. The urea-urethane solutions obtained in this way are used as rheology control agents in liquid polymer systems.

Patent specification EP 1 630 191 describes a process for producing (poly)urea powders by means of spray drying. The (poly)urea powders obtained may consist either of monourea compounds or of polyurea compounds, and preferably have a low molecular weight. These (poly)urea compounds preferably have only a few urea groups. The (poly)urea powders are intended for use in compositions which are said to be suitable as lubricants, thickeners and/or processing agents. For these purposes the (poly)urea powders are intended for dispersion into a base oil and/or solvent. During the preparation or the use, the (poly)urea particles are present in the form of a solid or suspension.

EP 2 931 771 discloses a composition that is effective as a rheology additive and contains 15 to 95% by weight of an oxygen compound, 5 to 75% by weight of a urea compound, 0 to 50% by weight of an ionogenic compound and 0 to 35% weight of an organic solvent. However, the sag resistance, particularly at high layer thicknesses still needs to be improved.

It was an object of the present invention, therefore, to provide new rheology control agents. These new agents ought not to have the disadvantages stated in the abovementioned specifications. More particularly the intention was to find rheology control agents having a pronounced anti-sag behavior. Particularly, a high layer thickness of applied coatings should result without sagging. This effect should be accompanied by a low increase of flow viscosity, as e. g. measured with a flow cup (e.g., DIN cup) method. Furthermore, the rheology control agents ought not to be tied to the medium to be thickened, such as the binder, but instead to be able to be added as a completed additive at any point in a process for producing formulations.

The new rheology control agents ought to be distinguished by a strong rheological activity. Moreover, they ought to be suitable for adjusting the sagging characteristics of coating systems, particularly clear coat compositions. Such clear coat compositions should preferably be suitable for automotive coating, including automotive OEM coating and automotive repair and refinish coating.

In systems comprising polar solvents such as alcohols and ketones, as well, the rheology control agents ought to exhibit good compatibility and a good rheological activity. With this class of substance, it ought to be possible to obtain rheology control agents for use in media with different polarities.

It is desirable, furthermore, for the new rheology agents to be easily obtainable and easy to process, it being an advantage if they are dust-free and can be incorporated without great cost or complexity into other systems. Moreover, they ought ideally to be transparent and to have no tendency to form bits in paints, for example. Such properties as high transparency and no tendency to form bits are particularly important in clear coat compositions for high quality coatings as required in the field of automotive OEM and repair/refinish coatings, where an influence on the transparency and gloss of the cured coating layer on the substrate must be minimized. In one particularly desirable embodiment, therefore, the rheology agents are to be in the form of a solution.

Surprisingly it has been found that these objects can be achieved by providing a urea group containing product comprising one or more species of formula (I)

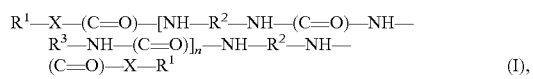

(I), wherein $R^1$ is independently selected from organic groups having 4 to 200 carbon atoms, preferably 4 to 150 carbon atoms and most preferred 4 to 100 carbon atoms,
X is O or $NR^4$, wherein $R^4$ is a hydrogen atom, an aliphatic group having 1 to 30 carbon atoms or an aromatic group having 6 to 30 carbon atoms,
$R^2$ is independently selected from hydrocarbyl groups having 4 to 40 carbon atoms,
$R^3$ is independently selected from hydrocarbyl groups having 2 to 40 carbon atoms, and wherein on average 76 to 100 mol % of all $R^3$ groups contained in the one or more species of formula (I) are hydrocarbyl groups having 2 or 3 carbon atoms, and
n is an integer of 2 to 150, preferably 2 to 100, more preferably 2 to 60, even more preferably 2 to 40 or 2 to 20, most preferably 2 to 10 or 3 to 10.

The term "urea group containing product" means any product, particularly any reaction product containing one or more of species of formula (I) defined as above. The average of 76 mol-% to 100 mol-% of all $R^3$ groups is calculated on the total number of moles of $R^3$ groups contained in the urea containing product of formula (I). Therefore, the proviso that on average 76 to 100 mol-% of the hydrocarbyl groups $R^3$ must be hydrocarbyl groups having 2 or 3 carbon atoms is satisfied even if the urea group containing product contains single species wherein no residues $R^3$ having 2 or 3 carbon atoms are contained if the collective of all species of formula (I) satisfy this requirement.

The term "organic group" means a carbon containing group selected from "aliphatic groups" and "aromatic groups", wherein the term "aliphatic group" encompasses non-aromatic, acyclic and cyclic, saturated and unsaturated carbon containing groups. However organic groups can also contain aliphatic and aromatic moieties at the same time. E.g. an aliphatic group which contains one or more aromatic groups as substituents is called araliphatic group. Of course, aromatic groups may comprise aliphatic substituents.

Organic groups may also contain one or more heteroatoms. Preferred heteroatoms are oxygen, nitrogen, sulfur and halide atoms. Most preferred heteroatoms are oxygen and nitrogen.

The term "hydrocarbyl groups" denotes for an organic group which consists of carbon and hydrogen atoms, only.
Species of Formula (I)
$R^1$ Groups
Groups $R^1$ are independently selected from organic groups having 4 to 200 carbon atoms, preferably 4 to 150 carbon atoms and most preferred 4 to 100 carbon atoms.

The $R^1$ groups are preferably aliphatic groups having 4 to 150 carbon atoms or aromatic groups having 6 to 150 carbon atoms. If $R^1$ contains aliphatic and aromatic moieties, $R^1$ is an araliphatic group, in case the atom in $R^1$ which is bound to X is not part of an aromatic moiety.

The term "aliphatic group" as used herein refers to a radical of an acyclic or cyclic, saturated or unsaturated carbon compound that does not contain aromatic structures (see: IUPAC Compendium of Chemical Terminology, 2nd Ed. (The "Gold Book") A. D. McNaught and A. Wilkinson, Blackwell Scientific Publications, Oxford (1997) XML online corrected version: http://goldbook.iupac.org (2006-) created by M. Nic, J. Jirat, B. Kosata; updates compiled by A. Jenkins, ISBN 0-9678550-9-8, https://doi.org/10.1351/goldbook). Accordingly, aliphatic groups or radicals may contain heteroatoms such as, for example, oxygen or nitrogen. As an example oxygen can be present in an aliphatic group in form of ether and/or ester groups. E.g. a polyoxyalkylene group is a heteroatom (in this case oxygen) containing aliphatic group.

Preferably $R^1$ is an aliphatic group having 4 to 150, more preferably 6 to 125 and most preferred 8 to 100 or 8 to 70 carbon atoms. Such aliphatic group $R^1$ can be saturated or unsaturated, branched or linear and can contain heteroatoms, particularly preferred oxygen atoms and/or nitrogen atoms as hetero atoms. Heteroatoms may be contained as single atoms, e.g. —O— or —S— forming ether groups or thio ether groups or in form of carbon and/or hydrogen containing functional groups as, e. g. ester groups, amide groups, carboxyl groups, amino groups or hydroxyl groups. If $R^1$ comprises functional groups which are reactive to isocyanate groups under the conditions of forming the urea group containing product, as e. g. amine groups and hydroxyl groups or carboxyl groups, these functional groups must be blocked with protective groups. The protective groups are removed after the urea group containing product formation reaction has run its course. Suitable blocking agents and measures for removing them are known to the skilled person. The amino groups may also be in salified or quaternized form. The carboxyl groups may likewise be in salified form.

In a preferred embodiment $R^1$ can be characterized by the following formula:

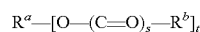

wherein
$R^a$ are independently from each other an aromatic hydrocarbyl group having 6 to 40 carbon atoms or an aliphatic hydrocarbyl group having 1 to 40 carbon atoms, more preferred a linear alkyl group having 1 to 40 carbon atoms or branched alkyl group having 3 to 40 carbon atoms or a linear or branched alkenyl group having 4 to 40 carbon atoms; in a very preferred embodiment, $R^a$ is selected from methyl, ethyl, n-propyl, isopropyl, n-butyl, isobutyl, n-hexyl, n-octyl, 2-ethylhexyl, n-decyl, isodecyl, n-undecyl, isoundecyl, n-dodecyl, isododecyl, n-tridecyl, isotridecyl, n-tetradecyl, isotetradecyl, n-pentadecyl, isopentadecyl, n-hexadecyl, n-octadecyl, oleyl;

$R^b$ are independently from each other
- a linear or branched alkylene group having 2 to 18, preferred 2 to 6, more preferred 2 to 5 carbon atoms; or
- a group $CHR^d$—$CHR^d$, wherein one $R^d$ is hydrogen and the other $R^d$ is selected from the groups consisting of
  - aromatic groups having 6 to 12 carbon atoms, preferably phenyl, and
  - groups of the formula $CH_2$—O—$(C=O)_m$—$R^e$, wherein
    - m=0 or 1 and
    - $R^e$ is an aliphatic group having 1 to 15, preferably 2 to 12, most preferred 2 to 10 carbon atoms or
    - an aromatic group having 6 to 20, preferably 6 to 12, most preferred 6 to 8 carbon atoms;

t=0 to 98, preferably 0 to 90, most preferred 0 to 80 or even 0 to 60; and independently from each other s=0 or 1 in the t residues [O—$(C=O)_s$—$R^b$];

with the proviso that the number of carbon atoms in $R^a$ plus the number of carbon atoms in the t residues [O—$(C=O)_s$—$R^b$] are
(i) from 4 to 200, if $R^a$ is aliphatic; and
(ii) from 6 to 200 if $R^a$ is aromatic.

If t=0, then $R^1$=$R^a$. in such case it is preferred that $R^a$ is an aromatic hydrocarbyl group having 6 to 20 carbon atoms or an aliphatic hydrocarbyl group having 4 to 50, more preferably 4 to 30 and most preferably 4 to 20 carbon atoms.

If t 1 and s=0, $R^1$ is a $R^a$ terminated ether residue (t=1) or polyether residue (t 2). In such case, it is preferred that the t residues [O—$R^b$] independently contain 2 to 8 carbon atoms, more preferred 2 to 4 or even 2 and/or 3 carbon atoms. If at least two different kinds of residues [O—$R^b$] are contained, they can be contained in any sequence, particularly a random sequence, a gradient sequence or in two or more blocks. Such ether groups can be formed by ring-opening addition or ring-opening addition polymerization of oxiranes to mono alcohols $R^a$—OH. Preferred oxiranes are ethylene oxide, propylene oxide and their mixtures. However other oxiranes as e. g. styrene oxide, glycidyl ether and glycidyl ester can also be used. If styrene oxide is used one $R^d$ in formula $CHR^d$—$CHR^d$ denotes for hydrogen, while the other $R^d$ denotes for phenyl. If a glycidyl ether is used one $R^d$ in formula $CHR^d$—$CHR^d$ denotes for hydrogen, while the other $R^d$ denotes for $CH_2$—O—$(C=O)_m$—$R^e$ with m=0. If a glycidyl ester is used, one $R^d$ in formula $CHR^d$—$CHR^d$ denotes for hydrogen, while the other $R^d$ denotes for $CH_2$—O—$(C=O)_m$—$R^e$ with m=1. In a preferred embodiment for s=0, $R^d$ is a linear or branched saturated hydrocarbyl group having 1 to 18, preferably 1 to 12, even more preferably 1 to 4 carbon atoms and $R^b$ is selected from ethylene and propylene groups.

If s=1, it is preferred that $R^b$ does not denote for $CHR^d$—$CHR^d$, but a linear or branched alkylene group as described above for $R^b$.

If t≥1 and s=1, $R^1$ is a $R^a$ terminated ester residue (t=1) or polyester residue (t≥2). In such case, it is preferred that the t residues [O—$(C=O)_s$—$R^b$] independently contain 3 to 5 carbon atoms. If at least two different kinds of residues [O—$(C=O)_s$—$R^b$] are contained, they can be contained in any sequence, particularly a random sequence, a gradient sequence or in two or more blocks. Such ester groups can be formed by ring-opening polymerization of lactones to using mono alcohols $R^a$—OH as chain starters. Preferred lactones are epsilon-caprolactone and delta-valerolactone and their mixtures.

If t≥2 and in at least one of residues [O—$(C=O)_s$—$R^b$] s=1 and in at least one further residue [O—$(C=O)_s$—$R^b$] s=0, than ether and ester groups are contained in $R^1$. Both types of groups can be distributed randomly. However, if for two or more residues s=1 and for two or more residues s=0, it is preferred, that those residues for which s=1 form one or more blocks and those residues for which s=0 also form one or more blocks. Within each of the blocks a random, gradient or block architecture can be realized.

X Groups

Groups X are selected from O and $NR^4$ groups, wherein $R^4$ is a hydrogen, an aliphatic group having 1 to 30 carbon atoms, preferably 1 to 20, more preferably 1 to 10 and most preferably 1 to 7 carbon atoms or an aromatic group having 6 to 30 carbon atoms, preferably 6 to 20, more preferably 6 to 10 and most preferably 6 or 7 carbon atoms.

If $R^4$ is an aliphatic group, it is most preferably a hydrocarbyl group containing the number of carbon atoms as defined in the previous paragraph. If $R^4$ is an aromatic group, it is most preferably a hydrocarbyl group containing the number of carbon atoms as defined in the previous paragraph. Most preferably $R^4$ is hydrogen.

Preferably X denotes for O or NH, most preferably O.

$R^2$ Groups

Groups $R^2$ are independently selected from hydrocarbyl groups having 4 to 40 carbon atoms, preferably 5 to 20, more preferred 6 to 15, most preferred 7 to 13 carbon atoms. The hydrocarbyl groups $R^2$ are aromatic or aliphatic. In case of aliphatic hydrocarbyl groups, cycloaliphatic hydrocarbyl groups are preferred. The $R^2$ groups are divalent groups since they are only bound to the adjacent NH groups of the species of formula (I).

Preferred groups $R^2$ are selected from

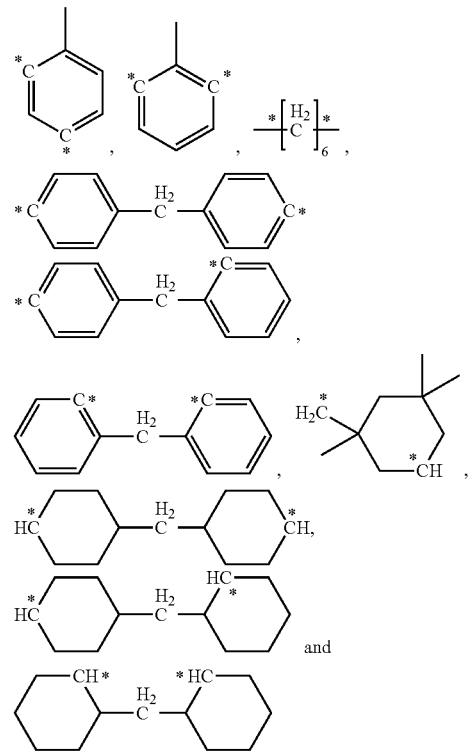

wherein the asterisk symbol * denotes the positions where $R^2$ is bound to the adjacent NH groups in the species of formula (I). From the above groups the most preferred groups are toluylene groups (2,4- and 2,6-isomers and mixtures thereof) and the 3-methylen-3,5,5-trimethylcyclohexyl group, under which toluylene groups, particularly the 2,4- and 2,6-isomers and mixtures thereof are utmost preferred.

$R^3$ Groups

Groups $R^3$ are independently selected from hydrocarbyl groups having 2 to 40 carbon atoms, preferably 2 to 20 carbon atoms, more preferred 2 to 12, most preferably 2 to 8 carbon atoms, with the proviso that on average 76 to 100 mol %, preferably 78 to 100 mol-%, more preferably 80 to 100 mol-% and even more preferably 84 or 85 to 100 mol-%, most preferably 90 to 100 or 95 to 100 mol % of all $R^3$ groups contained in the one or more species of formula (I) are hydrocarbyl groups having 2 or 3 carbon atoms, most preferably 2 carbon atoms. In a very special embodiment, 100 mol % of all $R^3$ groups contained in the one or more species of formula (I) are hydrocarbyl groups having 2 or 3 carbon atoms, most preferably 2 carbon atoms. Particularly preferred all $R^3$ groups are hydrocarbyl groups having two carbon atoms, i. e. are ethylene groups. The $R^3$ groups are divalent groups since they are only bound to the adjacent NH groups of the species of formula (I). If $R^3$ is a hydrocarbyl groups having 3 carbon atoms, $R^3$ can either be —$CH_2$—$CH_2$—$CH_2$—, —$CH_2CH(CH_3)$— or —$CH(CH_3)$—$CH_2$— under which the "methyl-substituted ethylene" groups —$CH_2CH(CH_3)$— or —$CH(CH_3)$—$CH_2$— are preferred. However, most preferred $R^3$ denotes for an unsubstituted ethylene group.

All before mentioned proviso percentage ranges apply irrespectively of the possibility that the group of hydrocarbyl groups having 2 or 3 carbon atoms, consists of hydrocarbyl groups having only 2 carbon atoms or consists of hydrocarbyl groups having only 3 carbon atoms or consists of a mixture of hydrocarbyl groups having 2 and 3 carbon atoms, respectively. Most preferred the before mentioned proviso percentage ranges apply in case the group of hydrocarbyl groups having 2 or 3 carbon atoms consists of —$CH_2$—$CH_2$— groups.

Examples of suitable $R^3$ groups are —$(CH_2)_p$— with $p=2$ to 20, preferably $p=2$ to 16 more preferably $p=2$ to 12, —$CH_2CH(CH_3)$—, —$CH_2C(CH_3)_2CH_2$—, the divalent radical 3-methylen-3,5,5-trimethylcyclohexyl as depicted for group $R^2$, the divalent radicals of cyclohexane, dicyclohexylmethane, 3,3'-dimethyl-dicyclohexylmethane, the para- and meta-xylylene radicals, the divalent radicals of diphenylmethane, 3,3-dimethyl-diphenylmethane and benzene.

Manufacture of the Urea Group Containing Products of the Invention

Briefly, the urea group containing product of the invention can be obtained by first reacting one or more components $R^1$—XH with one or more diisocyanates OCN—$R^2$—NCO to form one or more monoisocyanato adducts having the following formula (II)

$$R^1\text{—}X\text{—}(CO)\text{—}NH\text{—}R^2\text{—}NCO \qquad (II),$$

wherein $R^1$, $R^2$ and X are defined as above. This reaction is usually carried out with a molar excess of diisocyanates OCN—$R^2$—NCO to prevent the formation of by-products. The excess of diisocyanates OCN—$R^2$—NCO can be removed, e.g. by distillation, before carrying out the following second step. However, alternatively, it is possible to leave the excessive amount of diisocyanates OCN—$R^2$—NCO in the mixture, if at least some of the diisocyanates OCN—$R^2$—NCO used in the first step are the same as used in the second step. If the diisocyanates OCN—$R^2$—NCO used in the first step are the same as those used in the second step and if the excessive amount used in the first step equals the amount to be used for forming a mixture in the second step, i.e. the crude product obtained in the first step is the same as the mixture to be formed in the second step, the second step can even be skipped and it can directly be proceeded with the third step.

In a second step the one or more adducts of formula (II) are mixed with one or more diisocyanates OCN—$R^2$—NCO, wherein $R^2$ is defined as above to form a mixture.

In a third step this mixture is further reacted with one or more diamines $H_2N$—$R^3$—$NH_2$, wherein $R^3$ is defined as above to give a urea group containing product of the invention, containing one or more species of formula (I).

Stoichiometry

The value of n can be adjusted by the stoichiometry between species of formula (II), diisocyanates OCN—$R^2$—NCO and diamines $H_2N$—$R^3$—$NH_2$. The species of formula (II) will form the two terminal moieties of the species of formula (I). The molar ratio of diisocyanates OCN—$R^2$—NCO to diamines $NH_2$—$R^3$—$NH_2$ should approximately be m:(m+1) with m=n−1, n being defined as above. As an example, if 2 moles of OCN—$R^2$—NCO are mixed with 2 moles of the adduct according to formula (II), and if this mixture is reacted with 3 moles of $H_2N$—$R^3$—$NH_2$, i. e. m=2, a urea group containing product will be obtained wherein in average n will be 3. The higher the number of species of formula (II) and the lower the number of m, the lower the number average and weight average molecular weights of species of formula (I) will be.

Stabilizers

The reactions may take place in the presence of ionogenic compounds. As ionogenic compounds preferably salts are used containing cations of elements of the main groups I and II of the Periodic Table of the Elements (alkali and alkaline earth metals) or ammonium ions, preferably lithium, calcium or magnesium, particularly preferably lithium and calcium cations, and containing as anions preferably monovalent anions, particularly preferably halides, pseudohalides, formate, acetate and/or nitrate, most particularly preferably chloride, acetate and/or nitrate.

Particularly preferred as ionogenic compounds are soluble inorganic lithium salts, such as lithium chloride or lithium nitrate, for example. When ionic liquids are used as a carrier and/or solvent, it is possible to forego the use of the above stabilizers.

In the context of the present invention so-called ionic liquids (i.e. organic salts with a melting point 80° C.) are not subsumed under the term ionogenic compounds, but rather belong to solvents and/or carrier media.

The amount of ionogenic compound, preferably lithium compound is preferably 0.2 to 2.5, more preferably 0.1 to 1.5 and even more preferably 0.6 to 1.0 times the molar amount of the one or more diamines $H_2N$—$R^3$—$NH_2$.

In the processes for preparing the polyureas of the invention it is advantageous to use lithium compounds or liquid salts, to increase the storage stability of the rheology control agent systems.

Solvents

The reaction is usually carried out in an aprotic polar organic solvent. Suitable solvents are selected from the group of amides, preferably cyclic amides (i. e. lactams), and sulfoxides, preferably dimethyl sulfoxide. Likewise ionic liquids, which are organic salts with a melting point ≤80° C. can be used instead of the before mentioned aprotic organic solvents or in combination with them. Further suitable aprotic solvents which can be used in the manufacture of the urea group containing products of the invention are listed in the section on liquid compositions as suitable carrier media for the rheology control agents. Particularly suitable are solvents selected from the group of N-alkyl-lactams, preferable N-alkyl butyrolactams and even more preferred N—$C_{1-6}$-alkyl-butyrolactams, like N-butyl-butyrolactam. The solvents can serve as a carrier medium of the liquid compositions of the invention.

Reaction Temperature and Time

The choice of the respective reaction conditions, such as reaction temperature, reaction time and dosing rates, are known to the skilled person and are illustrated in more detail in the working examples.

Reactants

Component $R^1$—XH

Suitable components $R^1$—XH are those, wherein $R^1$ and X are defined as above.

Organic group $R^1$ may comprise polar functional groups such as, for example, ether, ester or amide groups or heteroaromatic moieties. Also, present may be amine groups and hydroxyl groups, with these functional groups being blocked. Where carboxyl groups are present, they too may be blocked. The protective groups are removed after the urea group containing product formation reaction has run its course. Suitable blocking agents and measures for removing them are known to the skilled person. The amino groups may also be in salified or quaternized form. The carboxyl groups may likewise be in salified form. Preferably residue $R^1$ does not contain functional groups which are apt to react with isocyanate groups under the conditions of the formation of the urea containing product of the present invention, particularly preferred $R^1$ does not contain primary amino groups, secondary amino groups, hydroxyl groups and carboxyl groups.

$R^1$—OH

Specific examples of components $R^1$—XH wherein X is oxygen and $R^1$ is defined as above are saturated, linear, branched or cyclic aliphatic monoalcohols having 4 to 100 carbon atoms or aromatic monoalcohols having 6 to 100 carbon atoms.

Examples of such monoalcohols are n-butanol, 2-ethylhexanol, isotridecyl alcohol, Guerbet alcohols with a chain length of $C_{10}$ to $C_{24}$, oleyl alcohol, linoleyl alcohol, lauryl alcohol, stearyl alcohol, cyclohexanol or the alkyl-substituted derivatives thereof, and benzyl alcohol.

Particularly suitable for adjusting the polarity are the alkoxylation products of the alcohols recited above, in which case it is also possible to use lower alcohols such as methanol or allyl alcohol, for example, as a starter component for an alkoxylation, where the methyl and allyl groups are examples for groups $R^a$ as defined above. The polyethers thus prepared preferably comprise, among others, ethylene oxide units and/or propylene oxide units or less preferred butylene oxide units and styrene oxide units in the chain, and may have these units, particularly ethylene oxide units and propylene oxide units in any order, as e.g. randomly distributed, as a gradient or in blocks. To start the alkoxylation it is also possible to use aromatic alcohols such as phenols or substituted phenols like alkylphenols, for example, as a starting component.

To adapt the compatibility of the urea group containing products of the invention to the formulations comprising them, it is also possible to introduce ester groups or polyester groups into the alcohol component, by reaction, for example, of lactones such as epsilon-caprolactone with the above-recited alcohols or alkoxylated alcohols.

Monoalcohols $R^1$—OH are preferred over the monoamines $R^1$—$NHR^4$, which are presented in the following.

$R^1$—$NHR^4$

Specific examples of components $R^1$—XH wherein X is $NR^4$, and $R^1$ and $R^4$ are defined as above are aliphatic monoamines which preferably are linear, branched or cyclic amines having 4 to 100 carbon atoms or aromatic monoamines having 6 to 100 carbon atoms.

Examples of such monoamines wherein $R^1$ is further defined to be a hydrocarbyl group are butyl amine, sec- and tert-butylamine, 3-methyl-1-butanamine, hexylamine, 2-ethylhexylamine, octyl-amine, cocoylamine, cyclopentylamine, cyclohexylamine, tridecylamine, oleylamine, octadecylamine, benzylamine, 2-phenylethylamine, 1-methylbenzylamine and the mixtures of $C_{12}$-$C_{22}$ amines that are known under the tradename Armeen from Akzo Nobel.

Examples are of such monoamines wherein $R^1$ contains heteroatoms are 2-ethoxyethylamine, 3-methoxy-1-propylamine, 1-methoxymethylpropylamine, 1,1-dimethoxy-2-propylamine, 3-ethoxy-1-propylamine, 3-butoxy-1-propylamine, 3-(2-ethylhexyloxy)-1-propylamine, 3-tridecyloxy-propylamine, 3-stearyloxypropylamine, p-methoxybenzylamine, 3,4-dimethoxybenzylamine, p-methoxyphenylethylamine, 3,4-dimethoxyphenylethylamine, 2-methyl-4-methoxyaniline, 2,5-dimethoxyaniline, furfurylamine, tetrahydrofurfurylamine, 2-(4-morpholinyl)ethylamine, 4-(3-aminopropyl)morpholine, 3- and (2-ethylhexyloxy) propylamine.

In accordance with the invention it is possible to use polyoxyalkylenemonoamines which contain alkylene oxide units, and particularly ethylene oxide units and/or propylene oxide units and which are for example known under the tradenames Jeffamine® M600, M1000, M2005, M2070, M2095, XTJ-435 and XTJ-436 from Huntsman.

Suitable secondary amines ($R^4 \neq H$) are, for example, diethylamine, dipropylamine, diisopropylamine, dibutylamine, diisobutylamine, dihexylamine, dioctylamine, dicyclopentylamine, dicyclohexylamine, ditridecylamine, dioctadecylamine or diphenylamine.

Diisocyanates OCN—$R^2$—NCO

Suitable diisocyanates OCN—$R^2$—NCO are those, wherein $R^2$ is defined as above.

Specific examples of such diisocyanates are 1,4-tetramethylene diisocyanate, 1,5-pentamethylene diisocyanate, 1,6-hexamethylene diisocyanate, 2,2,4-trimethyl-1,6-hexamethylene diisocyanate, 2,4,4-trimethyl-1,6-hexamethylene diisocyanate, 1,10-decamethylene diisocyanate, 1,4-cyclohexane diisocyanate, isophorone diisocyanate, p-phenylene diisocyanate, m-phenylene diisocyanate, 2,6-toluene diisocyanate, 2,4-toluene diisocyanate and mixtures thereof, p- and m-xylylene diisocyanate, α,α,α',α'-tetramethyl-1,3-xylylene diisocyanate, 4,4'-diisocyanatodicyclohexylmethane, 3,3'-dimethyl-4,4'-bisphenylene diisocyanate, 3,3'-dimethyl-diisocyanatodicyclohexylmethane, the isomer mixtures of 2,4'- and 4,4'-diisocyanatodiphenylmethane, and dimer diisocyanate, based on a dimerized fatty acid hydrocarbon backbone.

Diamines $H_2N$—$R^3$—$NH_2$

Suitable diamines $H_2N$—$R^3$—$NH_2$ are those, wherein $R^3$ is defined as above.

Specific examples of such diamines are e.g. acyclic aliphatic diamines as ethylenediamine, 1,2- and 1,3-propanediamine, 1,4-butanediamine, 1,5-pentanediamine, neopentanediamine, 1,6-hexamethylenediamine, 1,8-octamethylenediamine, 1,10-decamethylenediamine, 1,12-dodecamethylenediamine; cycloaliphatic diamines as cyclohexyldiamine, 4,4'-diaminodicyclohexylmethane, 3,3'- dimethyl-4,4'-diaminodicyclohexylmethane, isophorone-diamine; and araliphatic diamines like para- and meta-xylylenediamine or isomeric xylylenediamines; and aromatic diamines like 4,4-diaminodiphenylmethane, 3,3'-dimethyl-4,4'-diaminodiphenylmethane and isomeric phenylenediamines.

Preferred diamines are selected from ethylenediamine, 1,2-diaminopropane, and 1,3-diaminopropane. More preferred, the diamines are selected from ethylenediamine and 1,2-diaminopropane. The most preferred diamine is ethylenediamine, which contributes to the fulfillment of the proviso, that on average 76 to 100 mol-% of the hydrocarbyl groups $R^3$ must be hydrocarbyl groups having 2 or 3 carbon atoms.

Liquid Compositions Comprising the Urea Group Containing Product of the Invention The term "liquid composition" according to the present invention denotes a composition, i. e. a matter of at least two substances, being liquid, i. e. flowable at 23° C. and 100 kPa, wherein one of the at least two substances is the urea group containing product of the invention.

The term liquid composition as used herein also includes semi-finished products and final products, which themselves contain the rheology control agent comprising at least one urea group containing product of the invention, and preferably a carrier medium and a further ingredient which is different from the at least one urea group containing product of the invention and the carrier medium. An example for a semi-finished product is a mill base containing pigments and/or fillers and dispersants and the like, while an example for a final product is a coating composition containing such mill base.

The liquid composition of the invention may comprise constituents such as film-forming resins. Examples of film-forming resins are polyurethanes (1-component and 2-component systems), polyaspartics, polyacrylates, polyester resins, alkyd resins, and epoxy resins, PVC plastisols, PVC organosols, thermoplastics, and unsaturated polyester resins. Such liquid compositions are preferably converted into a solid state by usual thermal processes, but also other mechanisms, such as free-radical copolymerization or polyaddition, for example. Such liquid compositions are, for example, solventborne, aqueous, or solvent-free.

In the simplest case the liquid composition consists of the urea group containing product of the invention and a carrier medium. The carrier medium can be the solvent or mixture of solvents wherein the manufacture of the urea group containing product of the present invention was carried out. In such case, the liquid composition is preferably substantially clear to hazy, has preferably low- to medium-viscosity, forms a solution or dispersion having preferred active ingredient fractions, i. e. fractions of the urea group containing product of the invention from 5 to 70% by weight, more preferably 10 to 55% by weight, and most preferably 15 to 50% by weight or 20 to 45% by weight, based on the total weight of the liquid composition.

The liquid composition can e.g. be used as a rheology control agent which comprises at least one urea group containing product of the invention. Examples of carrier media are organic solvents, which may be polar or nonpolar. The urea group containing product may be present, for example, in solution or dispersion in the carrier medium. The rheology control agent itself may take the form of a solution, dispersion such as emulsion or suspension, gel or paste. Where the rheology control agent is to be in the form of a solution, it is preferred to use polar aprotic solvents.

Preferably, the rheology control agents according to the invention are present as a solution in aprotic organic solvents. Particularly suitable are polar, aprotic organic solvents, very particularly those which are selected from the group consisting of linear amides, lactams, sulfoxides and ionic liquids (i.e. organic salts with a melting point 80° C.). It is therefore preferred to use such solvents as carrier medium and/or to carry out the preparation of the inventive rheology control agents in these polar, aprotic organic solvents or ionic liquids.

Such a liquid composition preferably comprises or consists of
(a) 5 to 70% by weight of one or more urea group containing products according to the invention,
(b) 30 to 95% by weight of one or more polar aprotic solvents and/or ionic liquids, and
(c) 0 to 8% by weight of one or more ionogenic compounds, the amounts of (a), (b) and (c) being based on the total weight of the liquid composition.

More preferred, such a liquid composition comprises or consists of
(a) 10.0 to 55.0% by weight of one or more urea group containing products according to the invention,
(b) 44.8 to 89.8% by weight of one or more polar aprotic solvents and/or ionic liquids, and
(c) 0.2 to 6.0% by weight of one or more ionogenic compounds, the amounts of (a), (b) and (c) being based on the total weight of the liquid composition.

Even more preferred, such a liquid composition comprises or consists of
(a) 15.0 to 50.0% by weight of one or more urea group containing products according to the invention,
(b) 49.5 to 84.5% by weight of one or more polar aprotic solvents and/or ionic liquids, and
(c) 0.5 to 5.0% by weight of one or more ionogenic compounds, the amounts of (a), (b) and (c) being based on the total weight of the liquid composition.

Most preferred, such a liquid composition comprises or consists of
(a) 20.0 to 45.0% by weight of one or more urea group containing products according to the invention,
(b) 54.0 to 79.0% by weight of one or more polar aprotic solvents and/or ionic liquids, and
(c) 1.0 to 4.0% by weight of one or more ionogenic compounds, the amounts of (a), (b) and (c) being based on the total weight of the liquid composition.

Particularly preferred polar aprotic organic solvents are substituted or unsubstituted, preferably unsubstituted N-alkylbutyrolactams, dialkyl sulfoxides, substituted or unsubstituted amides, especially carboxamides. Examples of N-alkylbutyrolactams are N-methylbutyrolactam, N-ethylbutyrolactam, N-butylbutyrolactam, N-octylbutyrolactam and N-hydroxyethyl butyrolactam. An example of a dialkyl sulfoxide is dimethyl sulfoxide. Examples of linear amides are N,N-dimethylformamide, N,N-dimethylacetamide, N,N-dialkylamidoalkyl esters, N,N-dialkylamidoalkyl ethers, hexamethylphosphoric triamide and acylmorpholines. Preferred ionic liquids suitable as solvents are substituted imidazolium salts, e.g. 1-ethyl-3-methylimidazolium acetate, 1-ethyl-3-methylimidazolium acetate, 1-ethyl-3-methylimidazoliumethylsulfate, 1-butyl-3-methylimidazolium ethylsulfate, 1-ethyl-3-methylimidazolium thiocyanate and 1-butyl-3-methylimidazolium thiocyanate. The solvents and ionic liquids can also be used in combinations.

Among the solvents, preference is given to dimethylsulfoxide and, in particular, to such N-alkylbutyrolactams whose nitrogen-bonded alkyl radical is linear or branched, preferably linear, and the alkyl radical contains 1 to 20 or preferably 1 to 16, more preferably 1 to 12 and most preferably 3 to 10 carbon atoms, and also N,N-dimethylamidoalkyl ester, N,N-dimethylamidoalkyl ether, formylmorpholine and acetylmorpholine.

Depending on the application, those solvents are particularly preferred which have a corresponding miscibility with water, e.g. N-methylbutyrolactam, N-ethylbutyrolactam, N-propylbutyrolactam, N-butyl-butyrolactam, and dimethyl sulfoxide.

To enhance the solubilizing properties of the solvent or solvents used in liquid compositions, particularly liquid rheology control agents, ionogenic compounds can be used. As ionogenic compounds preferably salts are used containing cations of elements of the main groups I and II of the Periodic Table of the Elements (alkali and alkaline earth metals) or ammonium ions, preferably lithium, calcium or magnesium, particularly preferably lithium and calcium cations, and containing as anions preferably monovalent anions, particularly preferably halides, pseudohalides, formate, acetate and/or nitrate, most particularly preferably chloride, acetate and/or nitrate.

The rheology control agents which comprise at least one urea group containing product of the invention and preferably a carrier medium, can be easily incorporated into coating compositions and polymeric systems. Working with liquid compositions has the further advantages that they can be processed in dust-free form, are easily pumpable and dosable, are substantially transparent, exhibit particularly good compatibility with other systems, and do not produce bits in paints and coatings, for example.

The invention also relates to the use of the urea group containing products of the invention or the rheology control agents comprising those products for the rheology control of liquid composition which are in the form of semi-finished products and final products. Such liquid compositions are preferably selected from a coating composition, most preferred a clear coat composition, a plastic formulation, a pigment paste (e.g. an effect pigment paste), a sealant formulation, a cosmetic formulation, a ceramic formulation, an adhesive formulation or a liquid formulation for use in gas and oil production, a formulation for the manufacture of electrical components and circuits, a liquid formulation for use in energy storage media, a cleaning agent, a potting compound, a building material formulation, a lubricant, a filling compound, a wax emulsion, a metal-processing product, a metal-working fluid, a composition in the form of a spraying agent (for example as a so-called deposition aid in plant protection agents, or generally used for drift reduction), a printing ink or as an ink, for example an ink jet ink. The invention preferably relates to the liquid compositions comprising 0.05 to 10.00% by weight, preferably 0.10 to 8.00% by weight and even more preferred 0.20 to 5.00% by weight of the urea group containing products of the invention in form of a rheology control agent of the present invention, based on the total weight of the liquid composition according to the invention.

Particular preference is given to the use of the urea group containing products of the invention as a rheology control agent for the rheology control of coating compositions, particularly clear coat compositions.

In a particularly preferred embodiment of the present invention, the liquid composition containing the urea group containing product according to the present invention is a clear coat composition, preferably a 1-component or 2-component clear coat composition, most preferably a 2-component clear coat composition. A 2-component clear coat composition is a coating composition which cures by chemical reaction upon mixing a cross-linking component comprising a cross-linking agent with a base component comprising a polymeric binder. The cross-linking agent has reactive groups which react with reactive groups of the polymeric binder upon mixing the cross-linking component with the base component. Preferably the cross-linking agent is selected from the group of polyisocyanates, while the polymeric binder is preferably selected from the groups of polyols, most preferably polyester polyols, polyether polyol and poly(meth)acrylate polyols.

The 2-component clear coat compositions of the present invention are suitable in automotive OEM and repair coating applications, particularly as coating composition for refinish and repair coatings.

Yet another subject of the present invention is an article coated with a liquid composition, the liquid composition being a coating composition and even more preferably a clear coat composition such as a 1-component clear coat composition or 2-component clear coat composition as described above.

Further liquid compositions wherein the urea group containing products of the present invention and the rheology control additives of the present invention can be used are preferably solvent-based or solvent-free paints, printing inks and inks and lacquers as e.g. lacquers for varnishing of plastics, wire enamels, coating compositions for coating foodstuffs and seeds, and as so-called color resists, which are used for color filters, for example in flat panel displays such as liquid-crystal displays. The field of application lacquers also includes pasty materials which generally have a very high proportion of solids and a small proportion of liquid components, for example so-called pigment pastes or also pastes based on effect pigments, for example metal effect pigments such as, for example, aluminum pigments, silver pigments, brass pigments, zinc pigments, copper pigments, bronze pigments such as gold bronzes, fire-dyed bronzes or iron oxide aluminum pigments. The effect pigments also include, for example, interference pigments or pearlescent pigments such as, for example, metal oxide mica pigments, fish silver, bismuth oxide chloride or basic lead carbonate.

The plastic formulations can be (liquid) starting materials to produce plastic materials, which are preferably converted into a duromer by a chemical cross-linking process ("curing"). Preferred plastic preparations are unsaturated polyester resins, vinyl ester resins, acrylate resins, epoxy resins, polyurethane resins, formaldehyde resins (such as melamine-formaldehyde or urea-formaldehyde). These can be cured under very different conditions, e.g. at room temperature (cold-curing systems) or at elevated temperature (hot-curing systems), optionally with application of pressure ("closed mold" application, sheet molding compound or bulk molding compound). The plastic formulations also include PVC plastisols.

The cosmetic preparations can be various liquid compositions which are used in the so-called personal care or healthcare sector, e.g. lotions, creams, pastes such as, for example, toothpaste, foams such as, for example, shaving foam, gels such as, for example, shaving gels, shower gels or active ingredients in gel formulations, hair shampoos, liquid soaps, nail varnishes, lipsticks and hair dyes.

The so-called wax emulsions are preferably dispersions of solid waxes in particulate form at room temperature in water or an organic medium.

The building material formulations may be liquid or paste-like materials, which are used in the construction sector and solidify after curing. Examples are hydraulic binders such as concrete, cement, mortar, tile glue and plaster.

The metal working fluids may be cutting liquids, drilling fluids (such as are used in metal processing), release agents (often in the form of aqueous emulsions, for example, aluminum die casting and foundry applications), foundry washes (foundry coatings) and liquids for the surface treatment of metals (for example "surface finishing", surface treatment and plating).

The lubricants serve to reduce friction and wear, as well as to provide power, cooling, vibration dampening, sealing action and corrosion protection, liquid lubricants being preferred here.

The liquid formulations for use in gas and oil production are preferably oil-based fluids, which are used in the development of a deposit or also in the subsequent exploitation thereof (for example drilling, completion, stimulation, and production). Preference is given here to drilling muds, also referred to as drilling fluids. An application area for a corresponding formulation is, for example, the so-called "hydraulic fracturing". A further area of application is aqueous drilling muds.

Cleaning agents can be used to clean a wide range of objects. They effect or assist the removal of impurities, residues and attachments. The cleaners also include detergents (such as for cleaning textiles, their precursors, leather, and dishes), and personal care products.

The adhesives can be all adhesives materials which are liquid under processing conditions and which can join parts by surface adhesion and internal strength.

The rheology control agents are further useful as anti-settling agents, preferably for increasing the storage stability of compositions wherein they are used.

Any of the above liquid compositions of the invention may further comprise customary additives. Examples of additives are antiblocking agents, stabilizers, antioxidants, pigments, wetting agents, dispersants, emulsifiers, UV absorbers, free-radical scavengers, slip additives, defoamers, adhesion promoters, leveling agents, waxes, nanoparticles, film-forming auxiliaries, flame retardants and rheology additives which differ from the rheology control additives of the present invention. Preferred additives are wetting agents, dispersants and/or emulsifiers and rheology additives which differ from the rheology control additives of the present invention. Although the urea group containing product according to the invention provides excellent thickening properties, it is possible to use it in combination with other rheology control agents, if so desired. Examples of other rheology control agents include clay based thickeners (including organoclays), other urea compounds, (poly) amides, polysaccharides (like cellulose derivatives, guar, xanthan), polyacrylates, or associative thickeners. In a particular example, the urea group containing product of the invention can be used in combination with other thickeners affecting the low, medium, and/or high shear performance of the liquid composition that needs to be modified concerning its rheological behavior.

The urea group containing products of the invention are preferably used in such a way that in a liquid composition, where the liquid composition is a semi-finished or final product, there is preferably 0.05% to 10.00% by weight, more preferably 0.10% to 8.00% by weight, and very preferably 0.20% to 5.00% by weight, even more preferred 0.50% to 2.50% by weight of the urea group containing product, based on the total weight of the liquid composition.

The invention is illustrated further below referring to examples.

EXAMPLES

Synthesis Examples

TABLE 1

| Aromatic diisocyanates | | |
|---|---|---|
| Product name | Chemical Composition | Manufacturer |
| TDI T100 | 2,4-toluylene diisocyanate | Covestro AG |
| TDI T80 | 80/20 mixture of 2,4-toluylene diisocyanate and 2,6-toluylene diisocyanate | Covestro AG |
| TDI T65 | 65/35 mixture of 2,4-toluylene diisocyanate and 2,6-toluylene diisocyanate | Covestro AG |

Manufacture of Intermediates A1 to A4:

Diisocyanates were reacted with mono alcohols according to the procedure described in EP 1188779 to form mono-adducts (intermediates), containing one urethane group and one NCO group.

TABLE 2

| Intermediates | | |
|---|---|---|
| Intermediate | Mono alcohol | Diisocyanate |
| A1 | (Z)-Octadec-9-enol (oleic alcohol) | TDI T65 |
| A2 | Poly(ethylene oxide-co-propylene oxide (ratio EO:PO 1:1), starter:n-butanol, $M_n$ = 1300 g/mol | TDI T100 |
| A3 | Poly(ε-caprolactone), starter:isobutanol, $M_n$ = 750 g/mol | TDI T100 |
| A4 | Poly(ethylene oxide-co-propylene oxide (ratio EO:PO 1:1), starter:n-butanol, $M_n$ = 1300 g/mol | TDI T80 |

Step 1:

2 mol of the diisocyanate and 200 ppm benzoyl chloride were weighed into a glass flask equipped with stirrer, reflux condenser and nitrogen inlet and heated to 40° C. Subsequently 1 mol of the mono alcohol (according to the above table) was added dropwise to the reaction mixture over a period of 30 min. The reaction mixture was stirred for additional 5 hours at 60° C. A clear, light yellow, liquid crude intermediate containing excessive diisocyanate is obtained.

Step 2:

The excess of diisocyanate contained in the crude intermediates obtained in step 1 was removed by distillation, whereby intermediates A1 to A3 were obtained.

Comparative Examples C1 to C10 (Non-Inventive)

Completeness of the following reactions was evaluated with wet chemical methods by determination of NCO content and the amine value.

Comparative Rheology Additive C1:

In a glass flask with stirrer, reflux condenser and nitrogen inlet, 1.600 g (0.037 mol) lithium chloride were dissolved in 105 g N-butyl butyrolactam while stirring over a period of 30 min, whereby a clear solution was obtained. Subsequently 1.100 g (0.018 mol) ethylene diamine and 2.500 g (0.018 mol) m-xylylene diamine (m-XDA) were added and briefly homogenized. A uniform mixture of 35.600 g (0.024 mol) of adduct A2 and 4.300 g (0.024 mol) TDI T80 was added dropwise to the reaction mixture over a period of 25 min. The reaction mixture was stirred for additional 3 hours at 80° C. A slightly turbid, yellow, liquid product was obtained.

Comparative Rheology Additive C2:

In a glass flask with stirrer, reflux condenser and nitrogen inlet, 1.400 g (0.033 mol) lithium chloride were dissolved in 105 g N-butyl butyrolactam while stirring over a period of 30 min, whereby a clear solution was obtained. Subsequently 2.900 g (0.033 mol) 1,4-diaminobutane were added and briefly homogenized. A uniform mixture of 37.000 g (0.022 mol) of adduct A2 and 3.800 g (0.022 mol) TDI T80 was added dropwise to the reaction mixture over a period of 20 min. The reaction mixture was stirred for additional 3 hours at 80° C. A slightly turbid, yellow, liquid product was obtained.

Comparative Rheology Additive C3:

In a glass flask with stirrer, reflux condenser and nitrogen inlet, 1.400 g (0.033 mol) lithium chloride were dissolved in 105 g N-butyl butyrolactam while stirring over a period of 30 min, whereby a clear solution was obtained. Subsequently 3.800 g (0.033 mol) 1,6-diaminohexane were added and briefly homogenized. A uniform mixture of 37.500 g (0.022 mol) of adduct A2 and 3.800 g (0.022 mol) TDI T80 was added dropwise to the reaction mixture over a period of 20 min. The reaction mixture was stirred for additional 3 hours at 80° C. A clear, light brown, liquid product was obtained.

Comparative Rheology Additive C4:

In a glass flask with stirrer, reflux condenser and nitrogen inlet, 1.300 g (0.031 mol) lithium chloride were dissolved in 104.3 g N-butyl butyrolactam while stirring over a period of 30 min, whereby a clear solution was obtained. Subsequently 4.500 g (0.031 mol) 1,8-diaminooctane were added and briefly homogenized. A uniform mixture of 35.300 g (0.021 mol) of adduct A2 and 3.600 g (0.021 mol) TDI T80 was added dropwise to the reaction mixture over a period of 20 min. The reaction mixture was stirred for additional 3 hours at 80° C. A clear, light brown, liquid product was obtained.

Comparative Rheology Additive C5:

In a glass flask with stirrer, reflux condenser and nitrogen inlet, 1.500 g (0.036 mol) lithium chloride were dissolved in 105 g N-butyl butyrolactam while stirring over a period of 30 min, whereby a clear solution was obtained. Subsequently, 4.900 g (0.036 mol) m-xylene diamine were added and briefly homogenized. A uniform mixture of 34.400 g (0.024 mol) of adduct A2 and 4.200 g (0.024 mol) TDI T80 was added dropwise to the reaction mixture over a period of 30 min. The reaction mixture was stirred for additional 3 hours at 80° C. A clear, light brown, liquid product was obtained.

Comparative Rheology Additive C6:

In a glass flask with stirrer, reflux condenser and nitrogen inlet, 1.400 g (0.033 mol) lithium chloride were dissolved in 105 g N-butyl butyrolactam while stirring over a period of 30 min, whereby a clear solution was obtained. Subsequently 4.800 g (0.033 mol) 1,3-bis-aminomethyl cyclohexane were added and briefly homogenized. A uniform mixture of 34.900 g (0.022 mol) of adduct A2 and 3.900 g (0.022 mol) TDI T80 was added dropwise to the reaction mixture over a period of 35 min. The reaction mixture was stirred for additional 3 hours at 80° C. A turbid, yellow, liquid product was obtained.

Comparative Rheology Additive C7:

In a glass flask with stirrer, reflux condenser and nitrogen inlet, 1.400 g (0.033 mol) lithium chloride were dissolved in 105 g N-butyl butyrolactam while stirring over a period of 30 min, whereby a clear solution was obtained. Subsequently 6.300 g (0.033 mol) octahydro-4,7-methano-1H-indenedimethylamine were added and briefly homogenized. A uniform mixture of 33.600 g (0.022 mol) of adduct A2 and 3.700 g (0.022 mol) TDI T80 was added dropwise to the reaction mixture over a period of 20 min. The reaction mixture was stirred for additional 3 hours at 80° C. A clear, yellow, liquid product was obtained.

Comparative Rheology Additive C8:

In a glass flask with stirrer, reflux condenser and nitrogen inlet, 2.200 g (0.053 mol) lithium chloride were dissolved in 140 g N-butyl butyrolactam while stirring over a period of 30 min, whereby a clear solution was obtained. Subsequently 2.400 g (0.040 mol) ethylenediamine and 1.800 g (0.013 mol) m-xylylene diamine were added and briefly homogenized. The mixture became turbid. A uniform mixture of 47.500 g (0.035 mol) of adduct A2 and 6.100 g (0.035 mol) TDI T65 was added dropwise to the reaction mixture over a period of 20 min. During the addition, the reaction mixture cleared up completely. The reaction mixture was stirred for additional 3 hours at 80° C. A slightly turbid, yellow, liquid product was obtained.

Comparative Rheology Additive C9:

In a glass flask with stirrer, reflux condenser and nitrogen inlet, 2.300 g (0.053 mol) lithium chloride were dissolved in 140 g N-butyl butyrolactam while stirring over a period of 30 min, whereby a clear solution was obtained. Subsequently 2.400 g (0.040 mol) ethylendiamine and 1.200 g (0.013 mol) 1,4-diaminobutane were added and briefly homogenized. The mixture became turbid. A uniform mixture of 48.000 g (0.036 mol) of adduct A2 and 6.200 g (0.036 mol) TDI T65 was added dropwise to the reaction mixture over a period of 15 min. During the addition, the reaction mixture cleared up completely. The reaction mixture was stirred for additional 3 hours at 80° C. A slightly turbid, yellow, liquid product was obtained.

Comparative Rheology Additive C10:

In a glass flask with stirrer, reflux condenser and nitrogen inlet, 0.540 g (0.0128 mol) lithium chloride were dissolved in 105 g N-butyl butyrolactam while stirring over a period of 30 min, whereby a clear solution was obtained. Subsequently 0.770 g (0.0128 mol) ethylenediamine were added and briefly homogenized. The mixture became turbid. 42.930 g (0.0256 mol) of adduct A2 was added dropwise to the reaction mixture over a period of 25 min. During the addition, the reaction mixture cleared up completely. The reaction mixture was stirred for additional 3 hours at 80° C. A clear, light yellow, liquid product was obtained.

Examples (According to the Invention)

Completeness of the following reactions was evaluated with wet chemical methods by determination of NCO content and the amine value.

Rheology Additive According to the Invention E1:

In a glass flask with stirrer, reflux condenser and nitrogen inlet, 1.400 g (0.0332 mol) lithium chloride were dissolved in 105 g N-butyl butyrolactam while stirring over a period of 30 min, whereby a clear solution was obtained. Subsequently 2.000 g (0.0332 mol) ethylenediamine were added and briefly homogenized. The mixture became turbid. A uniform mixture of 37.800 g (0.0221 mol) of adduct A2 and 3.900 g (0.0221 mol) TDI T80 was added dropwise to the reaction mixture over a period of 25 min. During the addition, the reaction mixture cleared up completely. The reaction mixture was stirred for additional 3 hours at 80° C. A clear, light brown, liquid product was obtained.

Rheology Additive According to the Invention E2:

In a glass flask with stirrer, reflux condenser and nitrogen inlet, 2.100 g (0.049 mol) lithium chloride were dissolved in 140 g N-butyl butyrolactam while stirring over a period of 30 min, whereby a clear solution was obtained. Subsequently 2.900 g (0.049 mol) ethylenediamine were added and briefly homogenized. The mixture became turbid. 55.000 g of the product obtained in step 1 of the production of adduct A4 (containing 0.098 mol of excessive TDI; "crude intermediate") were added dropwise to the reaction mixture over a period of 30 min. During the addition, the reaction mixture cleared up completely. The reaction mixture was stirred for additional 3 hours at 80° C. A slightly turbid, yellow, liquid product was obtained.

Rheology Additive According to the Invention E3:

In a glass flask with stirrer, reflux condenser and nitrogen inlet, 1.900 g (0.0440 mol) lithium chloride were dissolved in 105 g N-butyl butyrolactam while stirring over a period of 30 min, whereby a clear solution was obtained. Subsequently 2.600 g (0.0440 mol) ethylenediamine were added and briefly homogenized. The mixture became turbid. A uniform mixture of 21.300 g (0.0147 mol) of adduct A2, 14.100 g (0.0147 mol) of adduct A3 and 5.100 g (0.0293 mol) TDI T80 was added dropwise to the reaction mixture over a period of 18 min. During the addition, the reaction mixture cleared up completely. The reaction mixture was stirred for additional 3 hours at 80° C. A clear, orange, liquid product was obtained.

Rheology Additive According to the Invention E4:

In a glass flask with stirrer, reflux condenser and nitrogen inlet, 2.200 g (0.0521 mol) lithium chloride were dissolved in 105 g N-butyl butyrolactam while stirring over a period of 30 min, whereby a clear solution was obtained. Subsequently 3.100 g (0.0521 mol) ethylenediamine were added and briefly homogenized. The mixture became turbid. A uniform mixture of 25.200 g (0.0174 mol) of adduct A2, 8.400 g (0.0174 mol) of adduct A1 and 6.000 g (0.0347 mol) TDI T80 was added dropwise to the reaction mixture over a period of 20 min. During the addition, the reaction mixture cleared up completely. The reaction mixture was stirred for additional 3 hours at 80° C. A clear, orange, liquid product was obtained.

Rheology Additive According to the Invention E5:

In a glass flask with stirrer, reflux condenser and nitrogen inlet, 2.000 g (0.047 mol) lithium chloride were dissolved in 140 g N-butyl butyrolactam while stirring over a period of 30 min, whereby a clear solution was obtained. Subsequently 2.800 g (0.047 mol) ethylenediamine were added and briefly homogenized. The mixture became turbid. A uniform mixture of 49.800 g (0.031 mol) of adduct A2 and 5.400 g (0.031 mol) TDI T65 was added dropwise to the reaction mixture over a period of 10 min. During the addition, the reaction mixture cleared up completely. The reaction mixture was stirred for additional 3 hours at 80° C. A slightly turbid, yellow, liquid product was obtained.

Rheology Additive According to the Invention E6:

In a glass flask with stirrer, reflux condenser and nitrogen inlet, 2.200 g (0.053 mol) lithium chloride were dissolved in 141.7 g N-butyl butyrolactam while stirring over a period of 30 min, whereby a clear solution was obtained. Subsequently 2.860 g (0.048 mol) ethylenediamine and 0.770 g (0.0057 mol) m-xylylenediamine were added and briefly homogenized. The mixture became turbid. A uniform mixture of 48.800 g (0.035 mol) of adduct A2 and 6.100 g (0.035 mol) TDI T65 was added dropwise to the reaction mixture over a period of 20 min. During the addition, the reaction mixture cleared up completely. The reaction mixture was stirred for additional 3 hours at 80° C. A clear, yellow, liquid product was obtained.

Rheology Additive According to the Invention E7:

In a glass flask with stirrer, reflux condenser and nitrogen inlet, 2.200 g (0.053 mol) lithium chloride were dissolved in 142.1 g N-butyl butyrolactam while stirring over a period of 30 min, whereby a clear solution was obtained. Subsequently 2.700 g (0.045 mol) ethylenediamine and 1.09 g (0.008 mol) m-xylylenediamine were added and briefly homogenized. The mixture became turbid. A uniform mixture of 48.800 g (0.035 mol) of adduct A2 and 6.100 g (0.035 mol) TDI T65 was added dropwise to the reaction mixture over a period of 20 min. During the addition, the reaction mixture cleared up completely. The reaction mixture was stirred for additional 3 hours at 80° C. A clear, yellow, liquid product was obtained.

Rheology Additive According to the Invention E8:

In a glass flask with stirrer, reflux condenser and nitrogen inlet, 2.200 g (0.053 mol) lithium chloride were dissolved in 141.05 g N-butyl butyrolactam while stirring over a period of 30 min, whereby a clear solution was obtained. Subsequently 3.020 g (0.050 mol) ethylenediamine and 0.360 g (0.0026 mol) m-xylylenediamine were added and briefly homogenized. The mixture became turbid. A uniform mixture of 48.800 g (0.035 mol) of adduct A2 and 6.100 g (0.035 mol) TDI T65 was added dropwise to the reaction mixture over a period of 20 min. During the addition, the reaction mixture cleared up completely. The reaction mixture was stirred for additional 3 hours at 80° C. A clear, yellow, liquid product was obtained.

Rheology Additive According to the Invention E9:

In a glass flask with stirrer, reflux condenser and nitrogen inlet, 2.200 g (0.053 mol) lithium chloride were dissolved in 141.1 g N-butyl butyrolactam while stirring over a period of 30 min, whereby a clear solution was obtained. Subsequently 2.860 g (0.048 mol) ethylenediamine and 0.490 g (0.0056 mol) 1,4-diaminobutane were added and briefly homogenized. The mixture became turbid. A uniform mixture of 48.800 g (0.035 mol) of adduct A2 and 6.100 g (0.035 mol) TDI T65 was added dropwise to the reaction mixture over a period of 15 min. During the addition, the reaction mixture cleared up completely. The reaction mixture was stirred for additional 3 hours at 80° C. A slightly turbid, yellow, liquid product was obtained.

TABLE 3A

Starting compounds for Producing Comparative Rheology Additives (used amounts in mol and (gram))

| | | | $H_2N$—$R^3$—$NH_2$ | | | | | Intermediate | $OCN$—$R^2$—$NCO$ | |
|---|---|---|---|---|---|---|---|---|---|---|
| Additives | D1 | D2 | D3 | D4 | D5 | D6 | D7 | A2 | TDI T80 | TDI T65 |
| C1 | 0.018 (1.100) | 0.018 (2.500) | | | | | | 0.024 (35.60) | 0.024 (4.30) | |

TABLE 3A-continued

Starting compounds for Producing Comparative Rheology Additives (used amounts in mol and (gram))

| | $H_2N-R^3-NH_2$ | | | | | | | Intermediate | $OCN-R^2-NCO$ | |
|---|---|---|---|---|---|---|---|---|---|---|
| Additives | D1 | D2 | D3 | D4 | D5 | D6 | D7 | A2 | TDI T80 | TDI T65 |
| C2 | | | 0.033 (2.900) | | | | | 0.022 (37.00) | 0.022 (3.80) | |
| C3 | | | | 0.033 (3.800) | | | | 0.022 (37.50) | 0.022 (3.80) | |
| C4 | | | | | 0.031 (4.500) | | | 0.021 (35.30) | 0.021 (3.60) | |
| C5 | | 0.036 (4.900) | | | | | | 0.024 (34.40) | 0.024 (4.20) | |
| C6 | | | | | | 0.033 (4.800) | | 0.022 (34.90) | 0.022 (3.90) | |
| C7 | | | | | | | 0.033 (6.300) | 0.022 (33.60) | 0.022 (3.70) | |
| C8 | 0.040 (2.400) | 0.013 (1.800) | | | | | | 0.035 (47.50) | | 0.035 (6.10) |
| C9 | 0.040 (2.400) | | 0.013 (1.200) | | | | | 0.036 (48.00) | | 0.036 (6.20) |
| C10 | 0.013 (0.770) | | | | | | | 0.026 (42.93) | | |

D1: ethylenediamine;
D2: m-XDA;
D3: 1,4-diaminobutane;
D4: 1,6-diaminohexane;
D5: 1,8-diaminooctane;
D6: 1,3-bis aminomethyl cyclohexane;
D7: octahydro-4,7-methano-1H-indenedimethylamine

TABLE 3B

Starting Compounds for Producing Rheology Additives According to the Invention (used amounts in mol and (gram))

| | $H_2N-R^3-NH_2$ | | | Intermediate | | | crude | $OCN-R^2-NCO$ | |
|---|---|---|---|---|---|---|---|---|---|
| Additives | D1 | D2 | D3 | A1 | A2 | A3 | A4 | TDI T80 | TDI T65 |
| E1 | 0.0332 (2.000) | | | | 0.0221 (37.80) | | | 0.0221 (3.90) | |
| E2 | 0.0490 (2.900) | | | | | | (55.00)-TDI T80 | 0.098 | |
| E3 | 0.0440 (2.600) | | | | 0.0147 (21.30) | 0.0147 (14.10) | | 0.0293 (5.10) | |
| E4 | 0.0521 (3.100) | | | 0.0174 (8.40) | 0.0174 (25.20) | | | 0.0347 (6.00) | |
| E5 | 0.0470 (2.800) | | | | 0.031 (49.80) | | | | 0.031 (5.40) |
| E6 | 0.0476 (2.860) | 0.0057 (0.770) | | | 0.035 (48.80) | | | | 0.035 (6.10) |
| E7 | 0.0450 (2.700) | 0.0080 (1.090) | | | 0.035 (48.80) | | | | 0.035 (6.10) |
| E8 | 0.0500 (3.020) | 0.0026 (0.360) | | | 0.035 (48.80) | | | | 0.035 (6.10) |
| E9 | 0.0476 (2.860) | | 0.0056 (0.490) | | 0.035 (48.80) | | | | 0.035 (6.10) |

D1: ethylenediamine;
D2: m-XDA;
D3: 1,4-diaminobutane

Application Examples and Testing

TABLE 4

Raw Materials

| Product name | Chemical Composition | Supplier |
| --- | --- | --- |
| Setal 1603 BA-78 | polyester polyol 78 wt.-% in butylacetate | Nuplex Resins B.V. |
| Setalux 1903 BA-75 | acrylate polyol 75 wt. % in butylacetate | Nuplex Resins B.V. |
| Butylacetat | n-butylacetate | Overlack GmbH |
| Dowanol PMA | 1,2-propanediol monoacetate monomethylether | Dow Chemical |
| Tinuvin 1130 | hydroxyphenylbenzotriazole (UV absorber) | BASF |
| Tinuvin 292 | bis- and methyl-(1,2,2,6,6-pentamethyl-4-piperidyl)-sebacate (light stabilizer) | BASF |
| TinStab BL 277 | dibutyltin dilaurate (catalyst) | Akcros Chemicals Ltd. |
| BYK-378 | leveling agent | BYK-Chemie GmbH |
| Tolonate HDT-LV | Solvent-free hexamethylene diisocyanate trimer | Vencore Chemicals JV |

Test System 1: 2-Component-PU Clear Coat for Automotive Repair

The clear coat composition was prepared according to the formulation shown in Table 5. 200 g of component A was weighed into a 870 ml polyethylene beaker and 8 g of a rheology control additive containing a species according to formula (I) was incorporated using a Dispermat CV (Getzmann) with a 4 cm tooth disk for 2 min at 1000 rpm. Subsequently, the samples were stored at room temperature for 48 hours. For the application, the addition of 100 g of component B was carried out by stirring with a spatula until the clear coat composition was optically homogeneous. The run-out time of the clear coat composition was then determined using a DIN 4 mm outlet beaker (BYK-Gardner GmbH). The clear coat composition was diluted with a solvent mixture (butylacetate/Dowanol PMA; 40:60 w/w) to the extent that it had a DIN 4 run-out time of 21 s (+/−1 s) for the application. The application of the clear coat composition was carried out by means of pneumatic spray application (LacTec paint shop, spray gun De VILBISS 797 "air cap", 1.3 mm nozzle, air flow speed: 0.6 m/s) on vertically suspended, primed and perforated steel plates (N/16300500L cold rolled fine sheet incl 16 holes a 10 mm with protective coating (gray/white, application side gray 300×500×0.60–0.70 mm) The clear coat composition was applied in three spray passes to determine the sag limit of the clear coat composition (the dry coat thickness of the clear lacquer was between 20-70 μm) After the spraying application, the coated sheets were vented vertically at room temperature for 10 minutes and then dried vertically at 60° C. for 60 minutes in a VTL 60/90 reflow oven (from Vötsch Industrietechnik GmbH). After 24 h the determination of the sag limit was made by optically determining that spot on the perforated plate, that had no clear coat accumulation under the hole (no distinct bead or runner formation). The determination of the dry layer thickness above and below the determined hole was carried out by means of a 3-fold measurement and the subsequent averaging with the dry-film measuring device Byko-Test 1500 (BYK-Gardner GmbH). The test results are shown in Table 6.

TABLE 5

2-component-PU clear coat composition

| Component | Product name | Amount in parts by weight |
| --- | --- | --- |
| A | Setal 1603 BA-78 | 45.8 |
|  | Setalux 1903 BA-75 | 109.4 |
|  | Butyl acetate | 23.4 |
|  | Dowanol PMA | 8.8 |
|  | Tinuvin 1130 | 2.9 |
|  | Tinuvin 292 | 0.8 |
|  | TinStab BL 277 (1 wt.-% in butyl acetate) | 8.8 |
|  | BYK-378 | 0.1 |
| B | Tolonate HDT-LV | 59.7 |
|  | Butyl acetate | 20.5 |
|  | Dowanol PMA | 19.8 |

TABLE 6

Results

| Clear Coat Composition | Rheology Additive | Sag limit [μm] |
| --- | --- | --- |
| 0 | Reference (no additive) | 28 |
| 1 | C1 | 30 |
| 2 | C2 | 37 |
| 3 | C3 | 29 |
| 4 | C4 | 31 |
| 5 | C5 | 39 |
| 6 | C6 | 28 |
| 7 | C7 | 28 |
| 8 | E1 | >67 |
| 9 | E2 | >69 |
| 10 | E3 | >60 |
| 11 | E4 | >57 |
| 12 | E5 | 64 |

In Table 6 it is clearly shown that surprisingly the non-inventive clear coat composition 0 (reference, no additive) as well as non-inventive clear coat compositions 1 to 7 (making use of non-inventive rheology additives C1 to C7) have a sag limit which is much lower than the sag limit of the inventive clear coat compositions 8 to 12 (making use of inventive rheology additives E1 to E5). Therefore the sag resistance of the inventive clear coat compositions is much higher compared to the non-inventive clear coat compositions.

Test System 2: 2-Component-PU Clear Coat for Automotive Repair

The clear coat composition used is the one according table 5. The clear coat compositions were prepared according to the same procedure as described for Test System 1. The rheology additives used are shown in table 7. Testing was carried out the same way as for Test System 1. The only difference to Test System 1 was that the spraying device for pneumatic spray application was changed to a spraying unit of Eisenmann LaTec GmbH (spray gun AGMD Pro (De Vilbiss), 1.2 mm nozzle De Vilbiss GTI PRO High Efficiency TE 40 C; air flow speed: 0.6 m/s). Results of the sag limit tests are shown in table 7.

TABLE 7

Results

| Clear Coat Composition | Rheology Additive | Sag limit [μm] |
| --- | --- | --- |
| 14 | Reference (no additive) | 25 |
| 15 | C8 | 33 |
| 16 | C9 | 34 |

TABLE 7-continued

Results

| Clear Coat Composition | Rheology Additive | Sag limit [μm] |
|---|---|---|
| 17 | E7 | 52 |
| 18 | E6 | 55 |
| 19 | E8 | >64 |
| 20 | E9 | >64 |
| 21 | C10 | 28 |

Table 7 shows that Comparative Rheology Additives C8 (making use of a mixture of 75 mol-% ethylenediamine and 25 mol-% of m-xylylenediamine in its manufacture) and C9 (making use of a mixture of 75 mol-% ethylenediamine and 25 mol-% of 1,4-diaminobutane in its manufacture) cause low sag limits in the respective, non-inventive clear coat compositions 15 and 16. If the molar ratio of ethylenediamine to m-xylylenediamine is increased to e.g. 85:15 (E7), 90:10 (E6) and 95:5 (E8) a much higher sag resistance is obtained for the clear coat composition. The same applies, if the molar ratio of ethylenediamine to 1,4-diaminobutane is increased to 90:10 (E9). Clear coat 21 demonstrates the Comparative Rheology Additive C10 causes a low sag limit. Comparative Rheology Additive C10 represents a urea group containing compound of formula (I), wherein n is 1.

The inventon claimed is:

1. A urea group containing product comprising one or more species of formula (I)

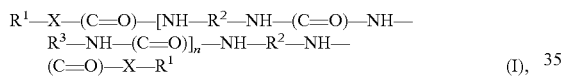

wherein $R^1$ independently represent an aliphatic group having 8 to 70 carbon atoms or a group of the formula $R^a$—[O—(C═O)$_s$—$R^b$]$_t$, wherein $R^a$ are independently from each other an aromatic hydrocarbyl group having 6 to 40 carbon atoms or an aliphatic hydrocarbyl group having 1 to 40 carbon atoms, $R^b$ are independently from each other a linear or branched alkylene group having 2 to 6 carbon atoms, t is 0 to 60, independently of each other, s is 0 or 1, with the proviso that the number of carbon atoms in $R^a$ plus the number of carbon atoms in the residues [O—(C═O)$_s$—$R^b$] are from 4 to 200 if $R^a$ is aliphatic and from 6 to 200 if $R^a$ is aromatic, X is O, $R^2$ independently represent hydrocarbyl groups having 6 to 15 carbon atoms, $R^3$ independently represent hydrocarbyl groups having 2 to 12 carbon atoms, and wherein on average 76 to 100 mol % of all $R^3$ groups contained in the one or more species of formula (I) are hydrocarbyl groups having 2 or 3 carbon atoms, and n is an integer of 2 to 40.

2. The urea group containing product according to claim 1, wherein at least 80 mol % of all $R^3$ groups are ethylene groups.

3. The urea group containing product according to claim 1, wherein $R^2$ independently represent any of

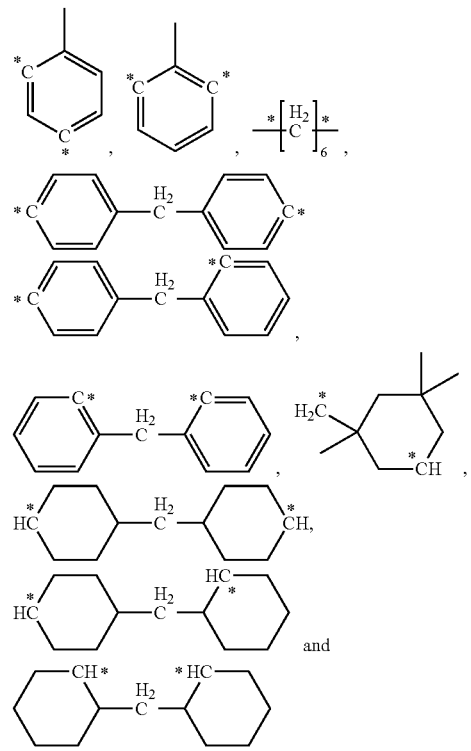

and the asterisk symbols (*) denote positions where $R^2$ is bound to adjacent NH groups in the species of formula (I).

4. A liquid composition comprising the urea group containing product according to claim 1 and a carrier medium.

5. The liquid composition according to claim 4, wherein the carrier medium comprises one or more of an amide, a sulfoxide, and an ionic liquid.

6. The liquid composition according to claim 4, wherein the liquid composition comprises:
 5 to 70% by weight of the urea group containing product,
 30 to 95% by weight of one or more of a polar aprotic solvent and an ionic liquid, and
 0 to 8% by weight of one or more ionogenic compounds, the amounts of (a), (b) and (c) being based on the total weight of the liquid composition.

7. A 2-component clear coat composition comprising:
 a carrier medium;
 a base component (A), containing the urea group containing product according to claim 1 and a polymeric binder having reactive groups; and
 a cross-linking component (B), containing a cross-linker having reactive groups, which are reactive towards the reactive groups of the polymeric binder in the base component (A).

8. A process for rheology adjustment, the process comprising adding the liquid composition according to claim 7 to one or more of a coating composition, a clear coat composition, a lacquer, a color resist, a plastic formulation, a pigment paste, an effect pigment paste, a sealant formulation, a wire enamel, a cosmetic formulation, a ceramic formulation, an adhesive formulation, a liquid formulation for use in gas and oil production, a liquid formulation for the manufacture of electrical components and circuits, a liquid formulation for use in energy storage media, a cleaning agent, a potting compound, a building material formulation, a lubricant, a filling compound, a wax emulsion, a metal-processing product, a metal-working fluid, a liquid formulation in the form of a spraying agent, a deposition aid, an ink, a printing ink and an ink jet ink.

9. The urea compound according to claim 1, wherein $R^a$ independently represent a linear alkyl group having 1 to 40 carbon atoms, a branched alkyl group having 3 to 40 carbon atoms, or a linear or branched alkenyl group having 4 to 40 carbon atoms.

10. A coating composition comprising:
a carrier medium;
a film forming resin; and
the urea group containing product according to claim 1.

11. The coating composition according to claim 10, further comprising a pigment.

12. A 1-component clear coat composition comprising:
a film forming resin;
a carrier medium; and
the urea group containing product according to claim 1.

13. A product comprising an article coated with the 2-component clear coat composition according to claim 7.

14. A product comprising an article coated with the coating composition according to claim 10.

15. A product comprising an article coated with the 1-component clear coat composition according to claim 12.

* * * * *